(12) United States Patent
Thomas et al.

(10) Patent No.: US 11,147,545 B1
(45) Date of Patent: Oct. 19, 2021

(54) CUTTING GUARD WITH GROUND CONNECTION

(71) Applicant: Covidien LP, Mansfield, MA (US)

(72) Inventors: Justin J. Thomas, New Haven, CT (US); Saumya Banerjee, Hamden, CT (US); Jacob C. Baril, Norwalk, CT (US); Matthew A. Dinino, Newington, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/900,257

(22) Filed: Jun. 12, 2020

(51) Int. Cl.
*A61B 17/02* (2006.01)
*A61B 17/34* (2006.01)

(52) U.S. Cl.
CPC ...... *A61B 17/0293* (2013.01); *A61B 17/3423* (2013.01); *A61B 2017/0287* (2013.01); *A61B 2217/002* (2013.01)

(58) Field of Classification Search
CPC ................ A61B 17/02; A61B 17/0218; A61B 2017/0225; A61B 17/3421; A61B 17/3423; A61B 17/3431; A61B 2017/3429
See application file for complete search history.

(56) References Cited

U.S. PATENT DOCUMENTS

| 5,312,391 | A | 5/1994 | Nilk |
| 5,403,311 | A | 4/1995 | Abele et al. |
| 5,458,598 | A | 10/1995 | Feinberg et al. |
| 5,556,397 | A | 9/1996 | Long et al. |
| 5,633,578 | A | 5/1997 | Eggers et al. |
| 5,814,044 | A | 9/1998 | Hooven |
| 5,919,202 | A | 7/1999 | Yoon |
| 6,086,583 | A | 7/2000 | Ouchi |
| 6,113,596 | A | 9/2000 | Hooven et al. |
| 6,379,350 | B1 | 4/2002 | Sharkey et al. |
| 6,387,094 | B1 | 5/2002 | Eitenmuller |
| 6,440,138 | B1 | 8/2002 | Reiley et al. |
| 6,565,560 | B1 | 5/2003 | Goble et al. |
| 7,041,101 | B2 | 5/2006 | Eggers |
| 7,232,440 | B2 | 6/2007 | Dumbauld et al. |
| 7,241,294 | B2 | 7/2007 | Reschke |
| 7,303,559 | B2 | 12/2007 | Peng et al. |
| 7,510,562 | B2 | 3/2009 | Lindsay |
| 7,537,594 | B2 | 5/2009 | Sartor |
| 7,588,570 | B2 | 9/2009 | Wakikaido et al. |

(Continued)

FOREIGN PATENT DOCUMENTS

| WO | 0101846 A2 | 1/2001 |
| WO | 2016014589 A1 | 1/2016 |

*Primary Examiner* — Eduardo C Robert
*Assistant Examiner* — Michelle C Eckman
(74) *Attorney, Agent, or Firm* — Carter, DeLuca & Farrell LLP

(57) ABSTRACT

A tissue guard for use with a surgical access device includes a proximal ring having proximal and distal ends, the distal end configured to operably couple to a ground ring that ultimately electrically connects to an electrical ground. One or more mechanical interfaces extend about the proximal ring and are configured to mechanically engage a rim of an access device to secure the tissue guard thereon. A retention body is configured to operably couple to a distal end of the ground ring, the retention body including a distal end configured to operably engage the access device to secure the tissue guard therein.

15 Claims, 9 Drawing Sheets

(56) References Cited

U.S. PATENT DOCUMENTS

| | | |
|---|---|---|
| 7,935,109 B2 | 5/2011 | Cosmescu |
| 8,267,928 B2 | 9/2012 | Orszulak et al. |
| 8,328,804 B2 | 12/2012 | Heard et al. |
| 8,454,600 B2 | 6/2013 | Huseman |
| 8,636,734 B2 | 1/2014 | Burbank et al. |
| 8,753,341 B2 | 6/2014 | Landry et al. |
| 8,808,287 B2 | 8/2014 | Heard et al. |
| 2002/0049442 A1 | 4/2002 | Roberts et al. |
| 2005/0059865 A1* | 3/2005 | Kahle .................. A61B 5/6898 600/206 |
| 2005/0187547 A1 | 8/2005 | Sugi |
| 2006/0095027 A1 | 5/2006 | Eggers |
| 2008/0015563 A1 | 1/2008 | Hoey et al. |
| 2009/0254084 A1 | 10/2009 | Naito |
| 2013/0178852 A1 | 7/2013 | Allen, IV et al. |
| 2013/0267947 A1 | 10/2013 | Orszulak |
| 2014/0031715 A1 | 1/2014 | Sherar et al. |
| 2016/0058495 A1 | 3/2016 | Twomey |

\* cited by examiner

CUTTING GUARD WITH GROUND CONNECTION

FIELD

The present disclosure relates to tissue specimen removal and, more particularly, to surgical access devices, tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically, a surgical sleeve and a specimen containment bag are used for this purpose. Moreover, during specimen rescission, smoke may cloud the operating site and may require evacuation therefrom. Smoke evacuation systems are commonplace for use with the surgical sleeve.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard for use with a surgical access device which includes a proximal ring having proximal and distal ends, an inner peripheral surface having one or more channels defined therein disposed in fluid communication with an operating cavity, and a plurality of fingers extending about the proximal ring, each finger configured to mechanically engage a rim of an access device to secure the tissue guard thereon. A ground connection assembly is configured to operably couple to the distal end of the proximal ring, the ground connection assembly including an electrically conductive ground ring disposed on an inner peripheral surface thereof electrically coupled to a ground wire configured for ultimate connection to an electrical ground. A retention body is included having proximal and distal ends, the proximal end of the retention body is configured to operably couple to the distal end of the ground connection assembly and the distal end includes a plurality of spaced-apart tabs extending therefrom configured to operably engage the access device to secure the tissue guard therein.

In aspects according to the present disclosure, the plurality of spaced-apart tabs of the distal end of the retention body each include a plurality of ridges defined therearound to facilitate retention of the tissue guard within the access device.

In aspects according to the present disclosure, the proximal ring includes an annular channel defined therein and a connection port disposed thereon in fluid communication with the annular channel and adapted to connect to a smoke evacuation system.

In aspects according to the present disclosure, the plurality of fingers each include a lower flange configured to operably engage the access device. In other aspects according to the present disclosure, the plurality of spaced-apart tabs are scalloped to facilitate engagement with the access device. In still other aspects according to the present disclosure, each of the spaced-apart, scalloped tabs includes a plurality of ridges disposed thereon to facilitate engagement with the access device.

In aspects according to the present disclosure, the proximal ring is resilient to facilitate mechanical engagement atop the access device.

Provided in accordance with aspects of the present disclosure is a tissue guard for use with a surgical access device which includes a proximal ring having proximal and distal ends, the distal end configured to operably couple to a ground ring that ultimately electrically connects to an electrical ground. One or more mechanical interface extends about the proximal ring and is configured to mechanically engage a rim of an access device to secure the tissue guard thereon. A retention body is included and is configured to operably couple to a distal end of the ground ring, the retention body including a distal end configured to operably engage the access device to secure the tissue guard therein.

In aspects according to the present disclosure, the retention body includes a plurality of spaced-apart tabs at a distal end thereof configured to facilitate retention of the tissue guard within the access device. In other aspects according to the present disclosure, the plurality of spaced-apart tabs each include a plurality of ridges defined therearound to facilitate retention of the tissue guard within the access device. In still other aspects according to the present disclosure, the plurality of spaced-apart tabs are scalloped to facilitate engagement with the access device.

In aspects according to the present disclosure, the proximal ring includes an annular channel defined therein and a connection port disposed thereon in fluid communication with the annular channel and adapted to connect to a smoke evacuation system.

In aspects according to the present disclosure, the proximal ring is resilient to facilitate mechanical engagement atop the access device.

In aspects according to the present disclosure, the tissue guard further includes a plurality of fingers extending about the proximal ring, each finger is configured to mechanically engage a rim of the access device to secure the tissue guard thereon. In other aspects according to the present disclosure, the plurality of fingers each include a lower flange configured to operably engage the access device

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1A:
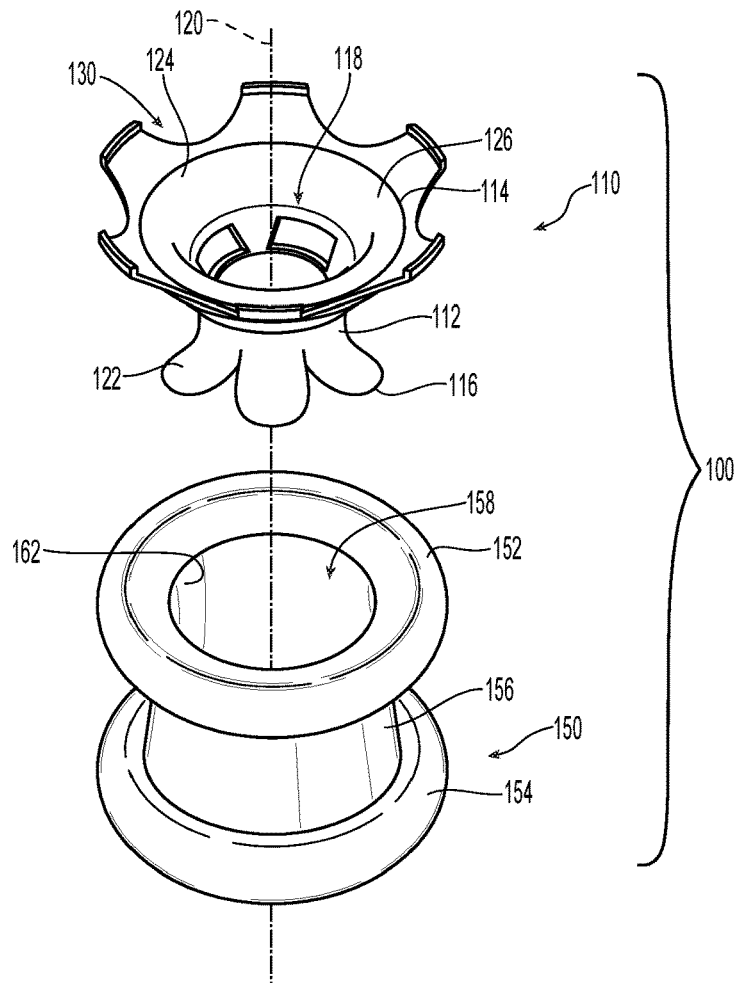
FIG. 1A is an exploded, top, perspective view of a prior art system including an access device and a tissue guard.
Figure 1B:
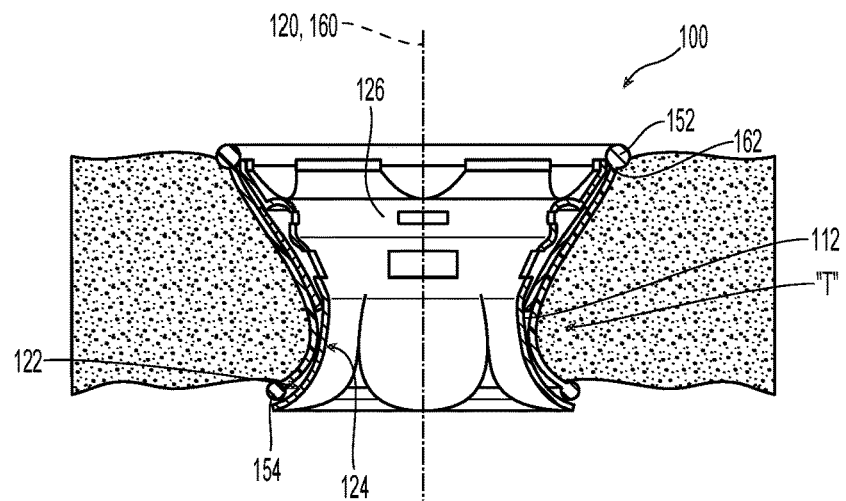
FIG. 1B is a cross-sectional view of the prior art system of FIG. 1A disposed within an opening in tissue.

Turning to FIGS. 1A and 1B, a prior art system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Figure 1C:
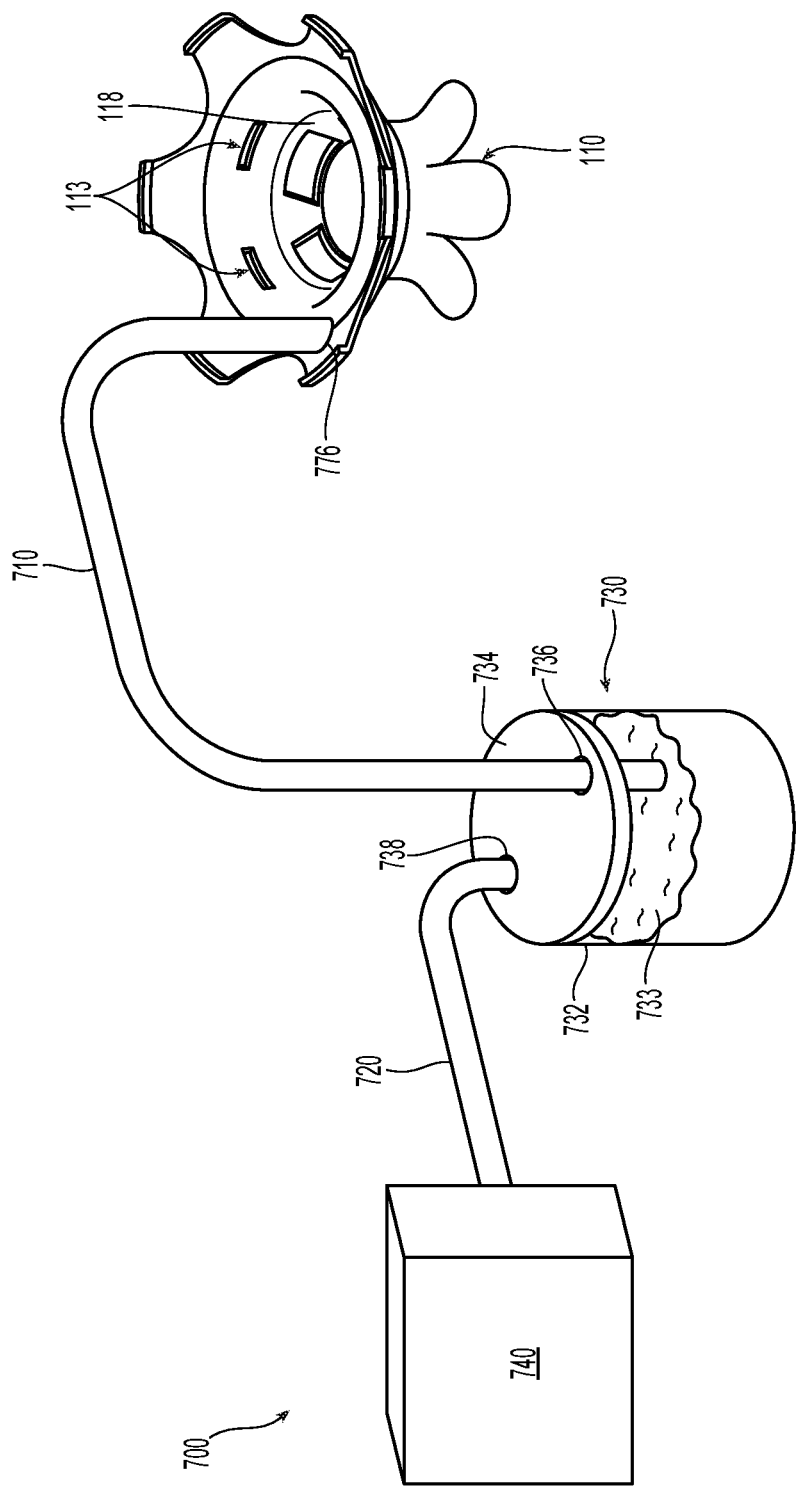
FIG. 1C is a schematic illustration of a smoke evacuation system for use with one or more of the access devices and tissue guards described herein.

Turning to FIG. 1C, smoke evacuation system 700 is provided in accordance with the present disclosure and is shown generally including tissue guard 110, tubing 710, 720, a collection reservoir 730, and a smoke evacuation (or vacuum) source 740. The various tissue guards disclosed herein are all designed to work with system 700. Tissue guard 110 and tubing 710 are detailed above and are coupled to one another, e.g., via engagement of one end of tubing 710 about exhaust connection 776 of tissue guard 710. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through lip 126 of tissue guard 110, tubing 710, collection reservoir 730, tubing 720, to smoke evacuation source 740. During use, this suction, in addition to evacuating smoke from tissue guard 110, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

Figure 2A:
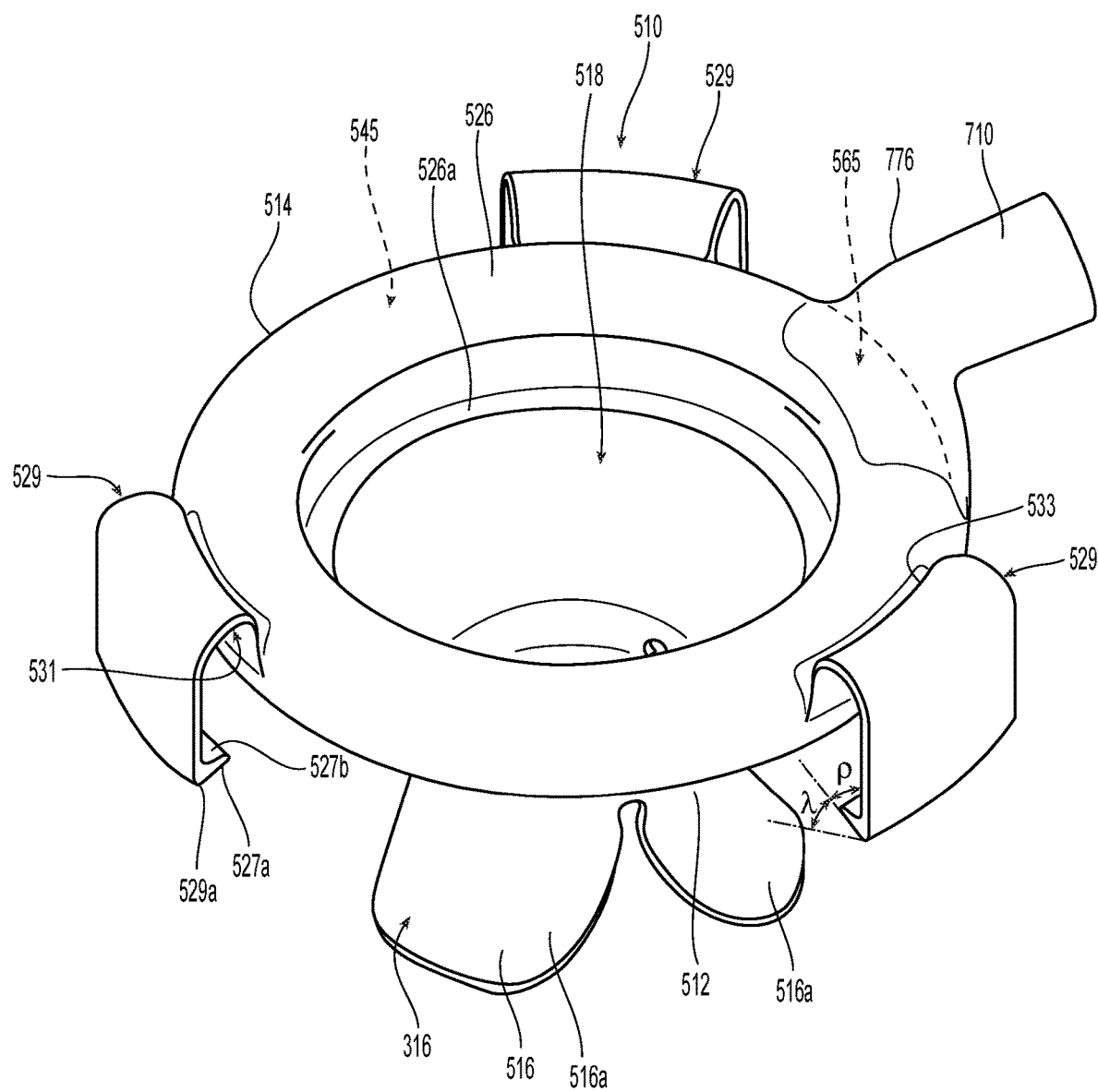
FIG. 2A is a top perspective view of a tissue guard for use with the access device.
Figure 2B:
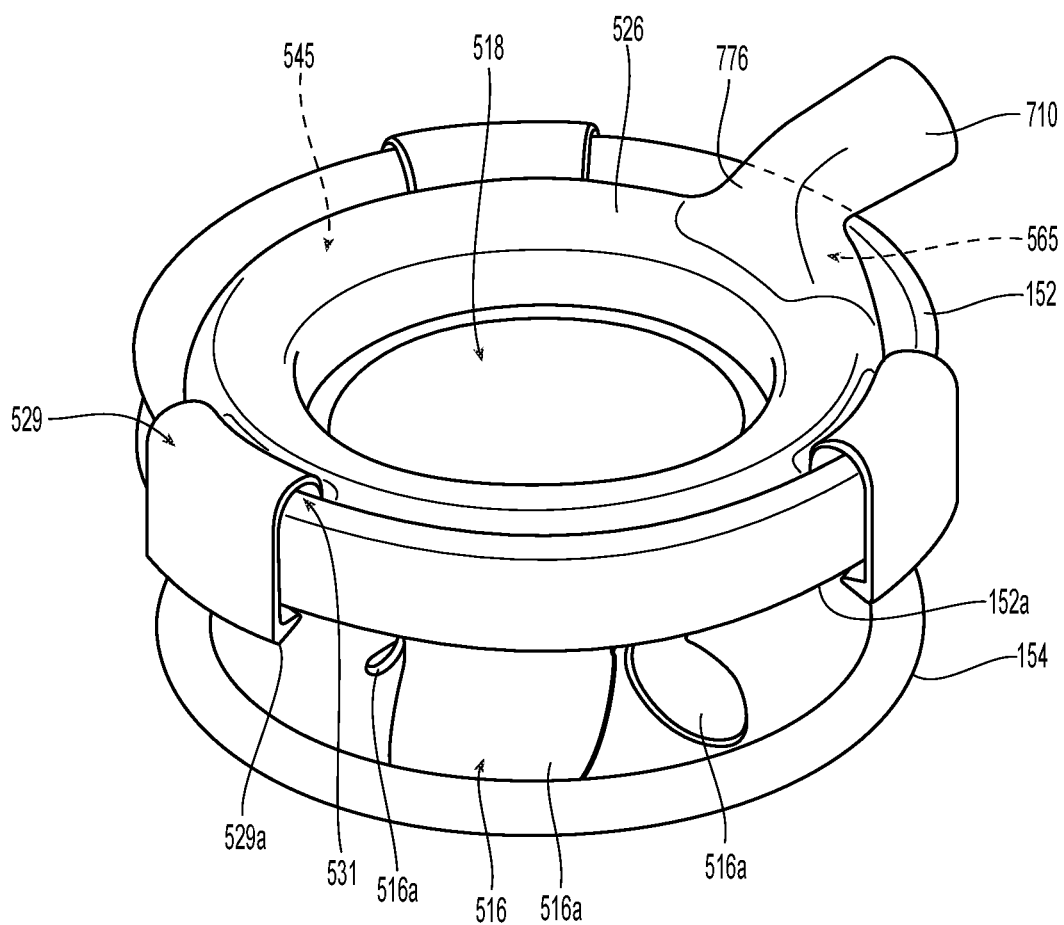
FIG. 2B is a top perspective view of the tissue guard of FIG. 2A engaged to a proximal rim of the access device.

Turning to FIGS. 2A-2B, another tissue guard 510 provided in accordance with the present disclosure is shown. Tissue guard 510 is similar to tissue guard 110 except as explicitly contradicted below and may be used in conjunction with access device 150 as part of a system similar to system 100. For purposes of brevity, only differences between tissue guard 510 and tissue guard 110 are detailed below, while similarities are summarily described or omitted.

Tissue guard 510 includes a body 512 defining an open proximal end 514, an open distal end 516, and a lumen 518 extending therebetween. A lip 526 extends radially outwardly from open proximal end 514 of body 512 and includes a plurality of fingers 529 extending from an outer peripheral surface thereof. The fingers 529 may be equidistantly-spaced about the lip 526 or may be spaced in any particular manner depending upon a particular purpose. In embodiments, a continuous finger (not shown) may be annularly spaced about the lip 526.

Each finger 529 includes an arcuate channel 531 defined along an inner peripheral surface thereof configured to at least partially encapsulate or mount atop rim 152 of the access device 150. More particularly, when the tissue guard 510 is first inserted into access device 150, channel 531 of each finger 529 aligns atop rim 152 of access device 150 and is poised for engagement atop rim 152 when the fingers 529 are secured. Each finger 529 also includes a flange 529a disposed at a distal end thereof that is configured to engage an underside of rim 152 to secure the tissue guard 510 in place. Finger 529 is configured to flex upon adaption of the tissue guard 510 onto access device 150 by virtue of rim 152 forcing flange 529a and finger 529 outwardly as the tissue guard 510 is inserted. Upon full insertion of the tissue guard 510 atop and into access device 150, the channel 531 of finger 529 encapsulates the rim 152 while the flange 529a snaps into place under rim 152 thereby locking the tissue guard 510 atop access device 150. The finger 529 is biased in the locked position. The flange 529a extends inwardly relative to the proximal ring 152 and operably engages the underside of the proximal ring 152 when biased.

Flange 529a may be angled to both facilitate insertion and to facilitate engagement. More particularly, an outer peripheral surface 527a of flange 529a may be disposed at a first angle lambda ($\lambda$) in the range from about 60 degrees to about 80 degrees to encourage the finger 529 and, hence, the tissue guard 510, to slip into lumen 118 and an inner peripheral surface 527b is disposed at second angle phi ($\gamma$) in the range from about 45 degrees to about 60 degrees to facilitate engagement of flange 529a with the underside of rim 152 (FIG. 2B). The shape of channel 531 may be dimensioned to conform to the shape of the outer peripheral surface of rim 152. Moreover, the height of the channel 531 may be dimensioned slightly larger than the thickness and depth of the rim 152 to facilitate engagement.

The distal end 516 of tissue guard 510 includes a plurality of scallop-like tabs 516a spaced-apart annularly thereabout. Scallop-like tabs 516a are configured engage an inner peripheral surface of body 112 of the access device 150 and are contoured or scalloped to generally mimic the shape thereof. The scallop-like tabs 516a are biased outwardly to maximize the opening at the distal end 516 of the tissue guard 510 and effectively secure the distal end 516 of the tissue guard 510 within access device 150 thereby facilitating surgical instrument access to the body cavity.

Figure 4A:
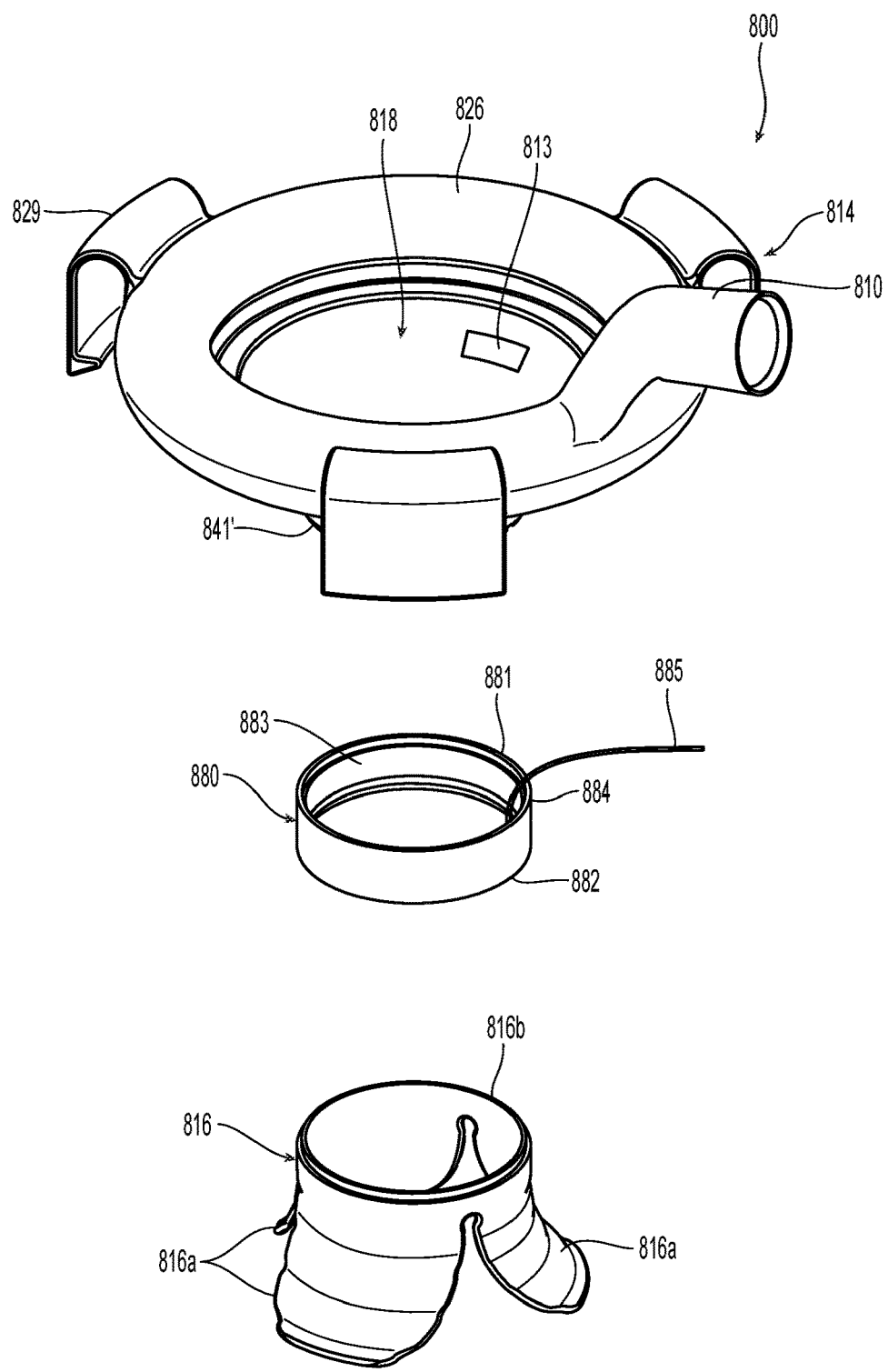
FIG. 4A is a top, exploded perspective view of the tissue guard of FIG. 3A including a funnel body, ground connection assembly and retention body.
Figure 4B:
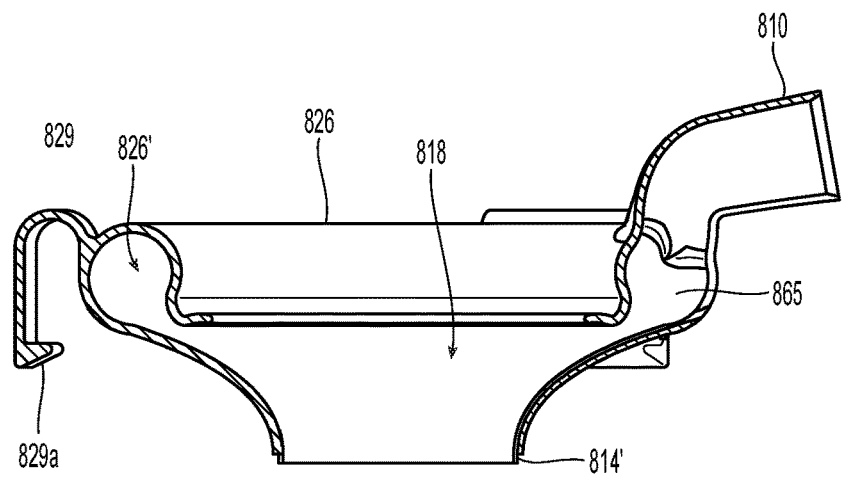
FIG. 4B is a side, cross sectional view of the funnel body of the tissue guard of FIG. 3A.

As mentioned above, lip 526 defines an annular channel therein configured to direct surgical exhaust therethrough to port 565 defined in an outer peripheral surface of lip 526. Lip 526 includes distal end 526a that extends inwardly therefrom towards lumen 518 to form annular channel 545 configured to direct surgical exhaust gas to port 565, respectively. One or more slits or passageways (passageways 113 of FIG. 1C or 813 of FIG. 4A) may be defined within the inner peripheral surface of distal end 526a that allow surgical gases passage into annular channel 545. As explained in more detail below, port 565 is configured to connect to an exhaust connection 776 of a fluid management or smoke evacuation system 700 (FIG. 1C). In other words, lip 526 is configured as generally hollow sleeves disposed proximate the inner peripheral surface of proximal end 514 of tissue guard 510 and is configured to direct evacuation fluids and smoke to the exhaust connection 776 and to the fluid management or smoke evacuation system 700.

Figure 3A:
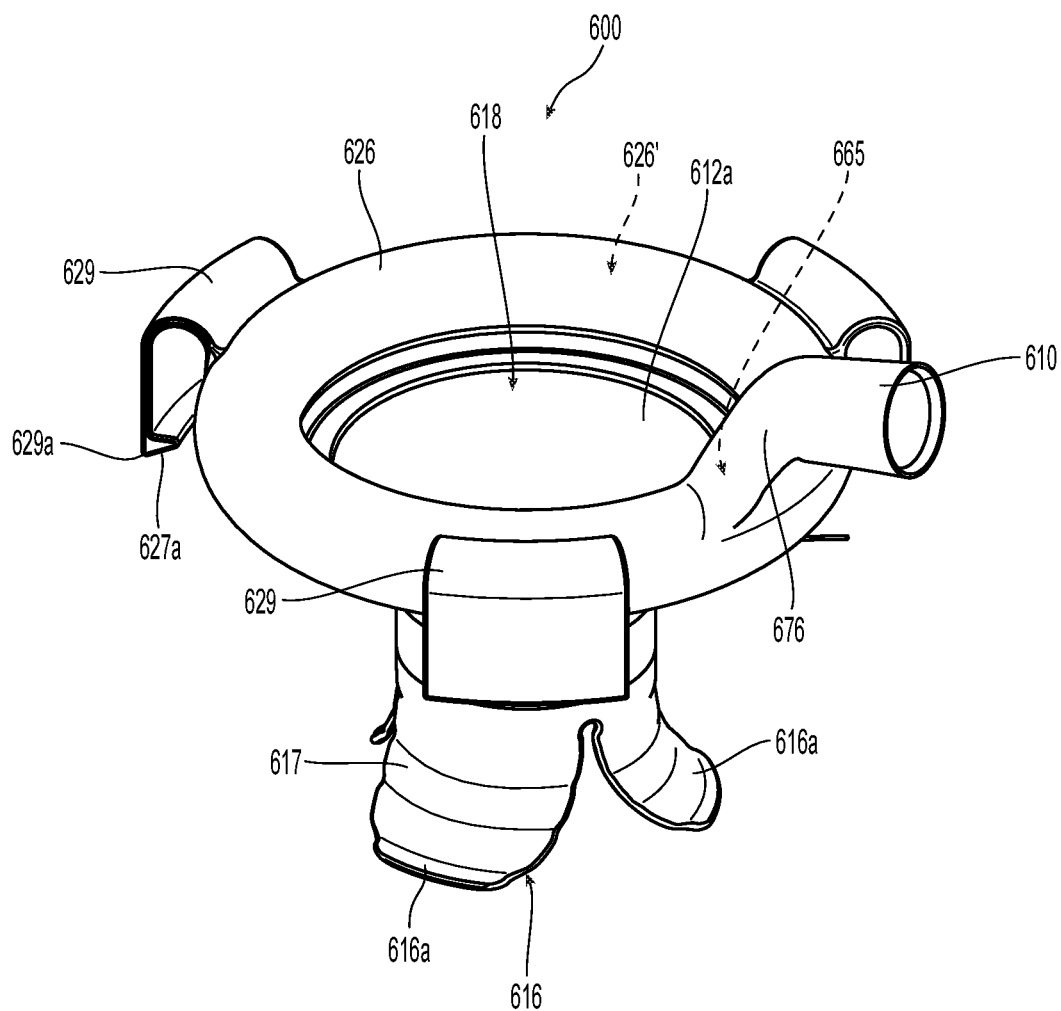
FIG. 3A is a top perspective view of one embodiment of a tissue guard for use with the access device in accordance with the present disclosure.
Figure 3B:
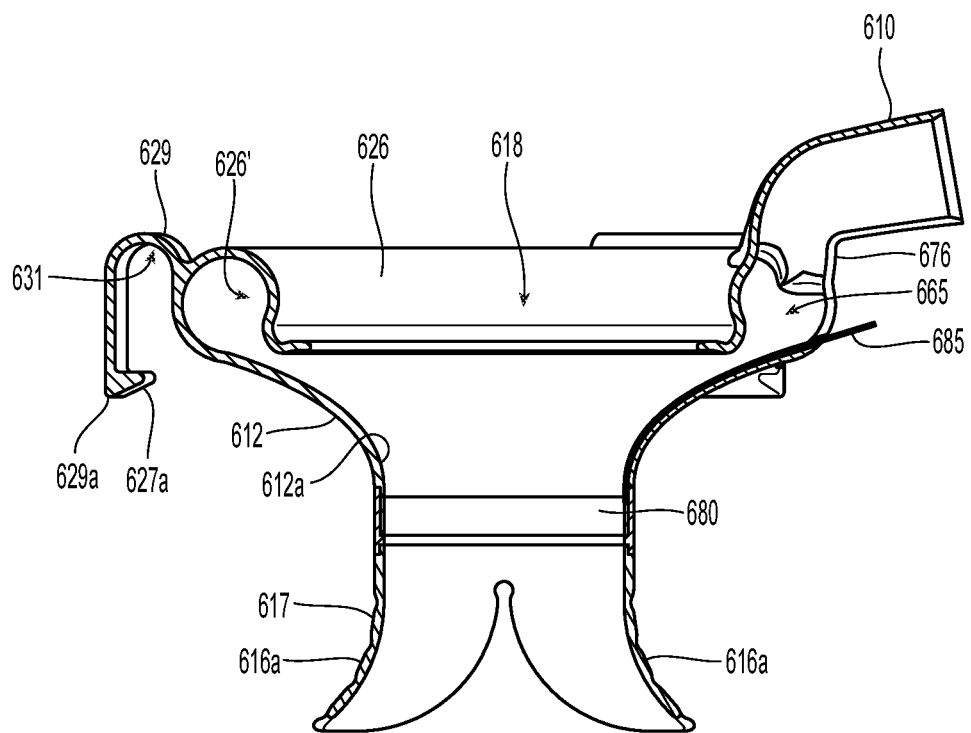
FIG. 3B is a side, cross sectional view of the tissue guard of FIG. 3A.

Turning to FIGS. 3A and 3B, one embodiment of a tissue guard is shown and is generally designated as reference numeral 600. Tissue guard 600 includes a body 612 and a proximal ring 626 that defines an annular channel 626' therein configured to convey smoke, odors and miscellaneous gases from the operating cavity to port 665 and then to smoke evacuation system 700 (FIG. 1C). More particularly, ring 626 is generally annular in shape and includes a connection port 676 that operably couples to tubing 710 of the smoke evacuation system 700. Ring 626 is configured to operably couple to the proximal rim 152 of access device 150 (similar to FIG. 2B) via one or more mechanically interfacing surfaces, fingers 629.

Each finger 629 includes an arcuate channel 631 defined along an inner peripheral surface thereof configured to at least partially encapsulate or mount atop rim 152 of the access device 150. More particularly, when the tissue guard 600 is first inserted into access device 150, channel 631 of each finger 629 aligns atop rim 152 of access device 150 and is poised for engagement atop rim 152 when the fingers 629 are secured. Each finger 629 also includes a flange 629a disposed at a distal end thereof that is configured to engage an underside of rim 152 to secure the tissue guard 600 in place. Finger 629 is configured to flex upon insertion of the tissue guard 600 into access device 150 by virtue of rim 152 forcing flange 629a and finger 629 outwardly as the tissue guard 600 is inserted. Upon full insertion of the tissue guard 600 into access device 150, the channel 631 of finger 629 encapsulates the rim 152 while the flange 629a snaps into place under rim 152 thereby locking the tissue guard 600 atop access device 150. The finger 629 is biased in the locked position. The flange 629a extends inwardly relative to the proximal ring 152 and operably engages the underside of the proximal ring 152 when biased.

Flange 629a may be angled or include angled surfaces similar to the angles described above with respect to FIGS. 2A and 2B to both facilitate insertion and to facilitate engagement. The shape of channel 631 may be dimensioned to conform to the shape of the outer peripheral surface of rim 152. Moreover, the height of the channel 631 may be dimensioned slightly larger than the thickness and depth of the rim 152 to facilitate engagement.

The distal end 616 of tissue guard 600 includes a plurality of scallop-like tabs 616a spaced-apart annularly thereabout. Scallop-like tabs 616a are configured engage an inner peripheral surface of body 112 of the access device 150 and are contoured or scalloped to generally mimic the shape thereof. The scallop-like tabs 616a are biased outwardly to maximize the opening at the distal end 616 of the tissue guard 600 and effectively secure the distal end 616 of the tissue guard 600 within access device 150 thereby facilitating surgical instrument access to the body cavity. The scallop-like tabs 616a each include ridges 617 defined therein and along the outer peripheral surface thereof to facilitate engagement with the inner peripheral surface 112 of access device 150.

A ground ring 680 is disposed along an inner peripheral surface 612a of lumen 618 of tissue guard 600 and is configured to operably connect to a ground wire 685 that extends along the inner peripheral surface 612a of lumen 618. Ground wire 685 is configured to extend from port 665 and to an electrical ground (not shown). Ground ring 680 acts as an auxiliary ground return during use of an electrosurgical pencil (not shown).

Turning to FIGS. 4A-4D, another embodiment of a tissue guard is shown and is generally designated as tissue guard assembly 800. Tissue guard assembly 800 is similar to tissue guard 600 and, as such, only those features that are different will be described in detail herein. Guard assembly 800 includes a body (not shown but similar to body 612) made from a series of assembled parts, namely, a proximal funnel body 814, a ground connection assembly 880, a distal retention body 816 and a lumen 818 defined therethrough.

Proximal funnel body 814 (FIG. 4B) includes a proximal ring 826 that defines an annular channel 826' therein configured to convey smoke, odors and miscellaneous gases from the operating cavity to port 865 and then to smoke evacuation system 700 (FIG. 1C) through tubing 810. One or more channels or slits 813 may be defined in the lumen 818 in fluid communication with the annular channel 826'. Ring 826 is resilient and configured to operably couple to the proximal rim 152 of access device 150 (similar to FIG. 2B) via one or more mechanically interfacing surfaces, e.g., fingers 829 and flanges 829a similar to the tissue guard 600 of FIGS. 3A-3B. Funnel body 814 includes a distal portion 814' that is configured to mechanically interface with a proximal portion 881 of the ground connection assembly 880 as explained in detail below.

Upon full insertion of the tissue guard 800 into access device 150, the finger 829 encapsulates the rim 152 and snaps into place under rim 152 thereby locking the tissue guard 800 atop access device 150.

Figure 4C:
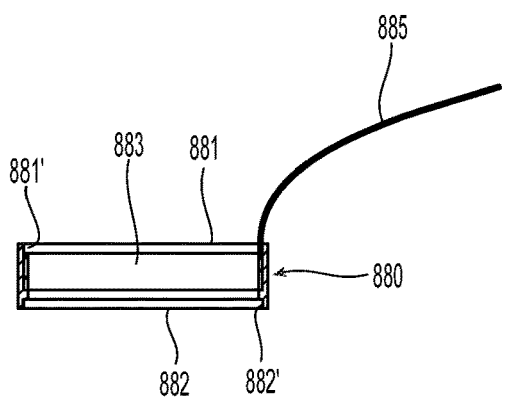
FIG. 4C is a side, cross sectional view of the ground connection assembly of the tissue guard of FIG. 3A.
Figure 4D:
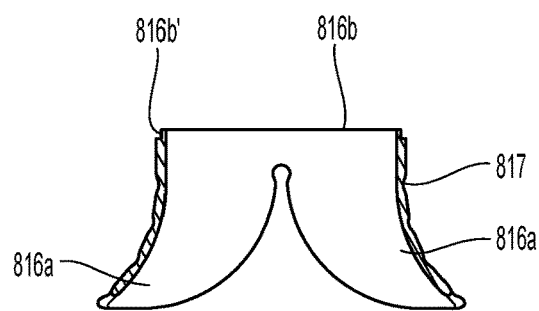
FIG. 4D is a side, cross sectional view of the retention body of the tissue guard of FIG. 3A.

The distal retention body 816 of tissue guard 800 includes a plurality of scallop-like tabs 816a spaced-apart annularly thereabout (FIG. 4D). Scallop-like tabs 816a are configured engage an inner peripheral surface of body 112 of the access device 150 and are contoured or scalloped to generally mimic the shape thereof. The scallop-like tabs 816a each include ridges 817 defined therein and along the outer peripheral surface thereof to facilitate engagement with the inner peripheral surface 112 of access device 150. A proximal portion 816b of the distal retention body 816 includes a mechanical interface 816b' configured to operably couple to a distal portion 882 of the ground connection assembly 880 as explained in more detail below.

Ground connection assembly 880 includes a ground body 884 having proximal and distal ends 881, 882, respectively (FIG. 4C). A ground ring 883 is disposed along an inner peripheral surface of body 884 and is configured to operably connect to a ground wire 885 that extends along the inner peripheral surface of lumen 618 to ultimately connect to an electrical ground. Ground ring 883 acts as an auxiliary ground return during use of an electrosurgical pencil (not shown).

As mentioned above, the proximal end 881 of ground body 884 includes a mechanical interface 881' that is configured to operably connect to the distal end 814' of the proximal funnel body 814 and the distal end 882 of the ground body 884 includes a mechanical interface 882' that is configured to operably connect to the proximal end 816b of the distal retention body 816 via mechanical interface 816b' of distal retention body 816. Once assembled and in use, the user inserts access device 150 into an operating cavity, inserts the tissue guard assembly 800 therein and then mounts the tissue guard assembly 800 atop the rim 152 of the access device 150. This secures all of the components for use. The user simply reverses the process to uncouple the tissue guard assembly 800 from the access device 150.

The tissue guard assembly 800 may be assembled during manufacturing or may be assembled on site. For example, the proximal funnel body 814, ground connection assembly and the distal retention body 816 may be aligned and assembled during the manufacturing process via glue, ultrasonic welding, screw-fit, snap-fit or any known mechanical connections in the art. Alternatively, the tissue guard assembly 800 may be sold as a kit and assembled on site utilizing simplified mechanical connections to assemble the various components, e.g., screw-fit, snap-fit, etc.

Figure 5:
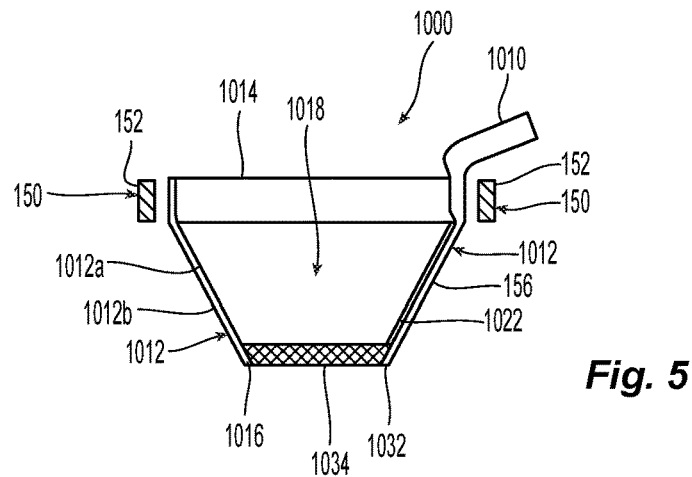
FIG. 5 is a side, cross-sectional schematic view of another embodiment of a tissue guard in accordance with the present disclosure.

FIG. 5 shows another embodiment of a tissue guard 1000 in accordance with the present disclosure. Tissue guard 1000 is similar to tissue guard 600 and, as such, only those features that are different will be described in detail herein. Tissue guard 1000 includes a body 1012 having a proximal end 1014, distal end 1016 and a lumen 1018 extending therebetween. Proximal end 1014 is configured to include tubing 1010 that ultimately connects to the smoke evacuation system 700.

Body 1012 is composed of an outer shell 1012a and an inner shell 1012b. A distal portion of the outer shell 1012a is coated with a conductive material 1032 around the inner peripheral surface thereof. Conductive material 1032 may be any conductive material or gel such as PolyHesive™ II hydrogel sold by Medtronic, Inc. The inner shell 1012b includes a series of pre-printed connectors 1034 disposed around the outer peripheral surface thereof that are configured to mechanically couple to the conductive material 1032 of the outer shell 1012a providing electrical continuity therebetween. Inner shell 1012b includes a ground wire 1022 that ultimately connects to an electrical ground. The combination of outer and inner shells 1012a, 1012b, when assembled, act as an auxiliary ground return during use of an electrosurgical pencil (not shown).

Figure 6A:
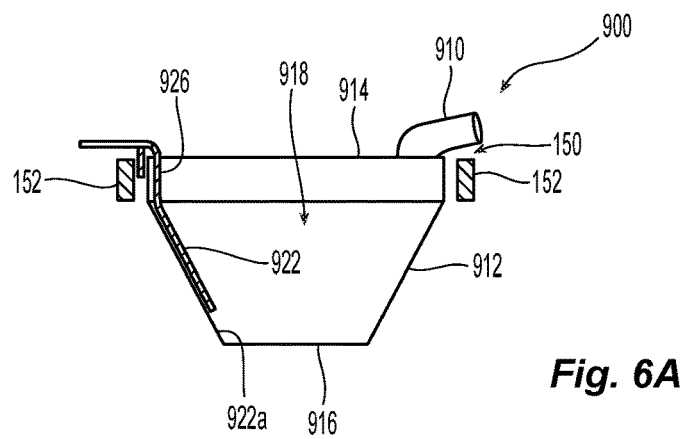
FIG. 6A is a side, cross-sectional schematic view of yet another embodiment of a tissue guard in accordance with the present disclosure including a clip-on ground return.
Figure 6B:
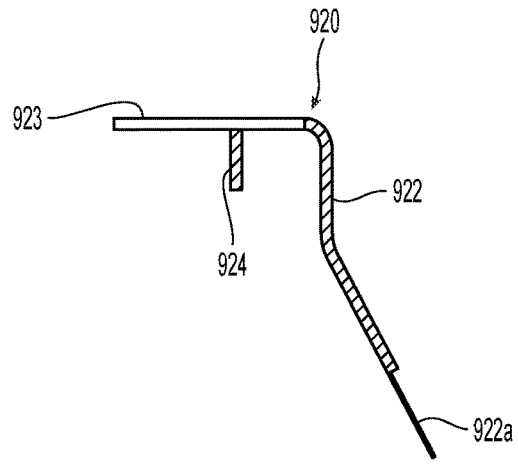
FIG. 6B is a side, cross-sectional schematic view of the clip-on ground return of FIG. 6A.

FIGS. 6A and 6B show another embodiment of a tissue guard ground clip 920 for use with known prior art tissue guards or any of the tissue guards described above. Tissue guard ground clip 920 may be used with any known tissue guard, e.g., similar to tissue guard 600 and, as such, only those features that are different will be described in detail herein. Tissue guard 900 includes a body 912 having a proximal end 914, distal end 916 and a lumen 918 extending therebetween. Proximal end 914 is configured to include tubing 910 that ultimately connects to the smoke evacuation system 700. Body 912 may be any standard tissue guard body such as those described above that is configured to mount atop an access device 150.

Ground clip 920 is configured to clip or otherwise securely mount atop the tissue guard 900 to act as an auxiliary return when using an electrosurgical pencil. More particularly, ground clip 920 includes a proximal mechanical interface 923 that mounts atop rim 152 of access device 150 and a flange 924 that depends from interface 923 that is configured to wedge between rim 152 of access device 150 and ring 926 of proximal end 914. Ground clip 920 also includes a plastic sheath 922 that extends into lumen 918 of tissue guard 900 along the inner peripheral surface thereof towards distal end 916. Sheath 922 is configured to house a conductive section 922a therein that extends therethrough. Conductive section 922a is exposed at a distal end of the sheath 922 and extends into the inner peripheral surface of the lumen 918. Conductive section 922a acts as an auxiliary ground return during use of an electrosurgical pencil (not shown).

Sheath 922 and the exposed conductive section 922a may be in the form of an elongated tube or strip or may be configured as an annular ring that extends around the inner peripheral surface of lumen 918. Mechanical interface 923 and flange 924 may be substantially annular, e.g., a continuous ring-like shape or a discontinuous ring-like shape. The flange 924 may be a series of flange-like tabs that extend around the mechanical interface 923 or vice versa.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard for use with a surgical access device, comprising:
    a proximal ring including proximal and distal ends;
        an inner peripheral surface having at least one channel defined therein disposed in fluid communication with an operating cavity;
        a plurality of fingers extending about the proximal ring, each finger configured to mechanically engage a rim of an access device to secure the tissue guard thereon;
    a ground connection assembly configured to operably couple to the distal end of the proximal ring, the ground connection assembly including an electrically conductive ground ring disposed on an inner peripheral surface thereof electrically coupled to a ground wire configured for ultimate connection to an electrical ground; and
    a retention body including proximal and distal ends, the proximal end of the retention body configured to operably couple to the distal end of the ground connection assembly, the distal end including a plurality of spaced-apart tabs extending therefrom configured to operably engage the access device to secure the tissue guard therein.

2. The tissue according to claim 1, wherein the plurality of spaced-apart tabs of the distal end of the retention body each include a plurality of ridges defined therearound to facilitate retention of the tissue guard within the access device.

3. The tissue according to claim 1, wherein the proximal ring includes an annular channel defined therein and a connection port disposed thereon in fluid communication with the annular channel and adapted to connect to a smoke evacuation system.

4. The tissue according to claim 1, wherein the plurality of fingers each include a lower flange configured to operably engage the access device.

5. The tissue according to claim 1, wherein the plurality of spaced-apart tabs are scalloped to facilitate engagement with the access device.

6. The tissue according to claim 5, wherein each of the spaced-apart, scalloped tabs includes a plurality of ridges disposed thereon to facilitate engagement with the access device.

7. The tissue according to claim 1, wherein the proximal ring is resilient to facilitate mechanical engagement atop the access device.

8. A tissue guard for use with a surgical access device, comprising:
    a proximal ring including proximal and distal ends, the distal end configured to operably couple to a ground ring that ultimately electrically connects to an electrical ground;
    at least one mechanical interface extending about the proximal ring configured to mechanically engage a rim of an access device to secure the tissue guard thereon; and
    a retention body configured to operably couple to a distal end of the ground ring, the retention body including a distal end configured to operably engage the access device to secure the tissue guard therein.

9. The tissue according to claim 8, wherein the retention body includes a plurality of spaced-apart tabs at a distal end thereof configured to facilitate retention of the tissue guard within the access device.

10. The tissue according to claim 9, wherein the plurality of spaced-apart tabs each include a plurality of ridges defined therearound to facilitate retention of the tissue guard within the access device.

11. The tissue according to claim 10, wherein the plurality of spaced-apart tabs are scalloped to facilitate engagement with the access device.

12. The tissue according to claim 8, wherein the proximal ring includes an annular channel defined therein and a connection port disposed thereon in fluid communication with the annular channel and adapted to connect to a smoke evacuation system.

13. The tissue according to claim 8, wherein the proximal ring is resilient to facilitate mechanical engagement atop the access device.

14. The tissue according to claim 8, further comprising a plurality of fingers extending about the proximal ring, each finger configured to mechanically engage a rim of the access device to secure the tissue guard thereon.

15. The tissue according to claim 14, wherein the plurality of fingers each include a lower flange configured to operably engage the access device.

* * * * *